(12) United States Patent
Renault

(10) Patent No.: US 8,914,960 B2
(45) Date of Patent: Dec. 23, 2014

(54) TOOTH BRUSH HEAD REMOVAL DEVICE

(75) Inventor: Gregory Owen Renault, Denver, CO (US)

(73) Assignee: Nina Nichols, LLC, Denver, CO (US)

( * ) Notice: Subject to any disclaimer, the term of this patent is extended or adjusted under 35 U.S.C. 154(b) by 615 days.

(21) Appl. No.: 13/124,639

(22) PCT Filed: Oct. 14, 2009

(86) PCT No.: PCT/ZA2009/000090
§ 371 (c)(1),
(2), (4) Date: Aug. 9, 2011

(87) PCT Pub. No.: WO2010/045661
PCT Pub. Date: Apr. 22, 2010

(65) Prior Publication Data
US 2011/0296658 A1   Dec. 8, 2011

(30) Foreign Application Priority Data

Oct. 15, 2008   (ZA) .................................. 2008/8793

(51) Int. Cl.
B23P 19/04       (2006.01)
B25B 27/14       (2006.01)
B23P 19/00       (2006.01)
A46B 17/00       (2006.01)
A61C 17/22       (2006.01)
A46B 7/04        (2006.01)

(52) U.S. Cl.
CPC ............... *A61C 17/222* (2013.01); *A46B 17/00* (2013.01); *A46B 7/04* (2013.01)
USPC ................... 29/264; 29/263; 29/256; 29/239; 29/278; 29/281.6; 29/426.1; 15/257.01

(58) Field of Classification Search
USPC ............... 29/402.01, 402.03, 402.08, 402.09, 29/402.11, 426.1, 426.5, 239, 244, 256, 29/263, 264, 265, 278, 281.6, 282; 15/257.01, 22.1
See application file for complete search history.

(56) References Cited

U.S. PATENT DOCUMENTS 3,858,300 A * 1/1975 Borel .............................. 29/256
4,899,430 A * 2/1990 Farino ............................ 29/240
5,247,716 A   9/1993 Bock
(Continued)

FOREIGN PATENT DOCUMENTS

WO   2008/014403 A2   1/2008

OTHER PUBLICATIONS

Non-Final Office Action, U.S. Appl. No. 11/495,291, Jan. 28, 2008, pp. 1-8.
International Search Report for PCT/US07/74489, International Searching Authority, Sep. 2, 2008, pp. 1-4.
(Continued)

*Primary Examiner* — Essama Omgba
(74) *Attorney, Agent, or Firm* — Samuel M. Freund; Cochran Freund & Young LLC

(57) ABSTRACT

A device (10) for removing the tooth brush head from the body of an electrical tooth brush is described. Device (10) includes a tooth brush head engaging member (12), a seat member (14) for seating against a body of an electrical-tooth brush and a screw-threaded member (16) positioned operatively between the tooth brush head engaging member (12) and the seat member (14), so as to cause the tooth brush head engaging member (12) to displace relative to the seat member (14) in response to angular displacement of the screw-threaded member (16).

6 Claims, 4 Drawing Sheets

(56) References Cited

U.S. PATENT DOCUMENTS

| | | | |
|---|---|---|---|
| 7,000,299 B2* | 2/2006 | Samchisen | 29/239 |
| 7,784,144 B2* | 8/2010 | Renault | 15/257.01 |
| 2003/0226223 A1 | 12/2003 | Chan | |
| 2004/0134057 A1* | 7/2004 | Samchisen | 29/426.5 |
| 2005/0273951 A1 | 12/2005 | Karl | |
| 2008/0028587 A1* | 2/2008 | Renault | 29/402.01 |

OTHER PUBLICATIONS

Non-Final Office Action, U.S. Appl. No. 11/495,291, Feb. 5, 2009, pp. 1-7.
Non-Final Office Action, U.S. Appl. No. 11/495,291, Oct. 20, 2009, pp. 1-8.
Final Office Action, U.S. Appl. No. 11/495,291, Apr. 5, 2010, pp. 1-8.
International Search Report, pp. 1-14, Feb. 10, 2010.

* cited by examiner

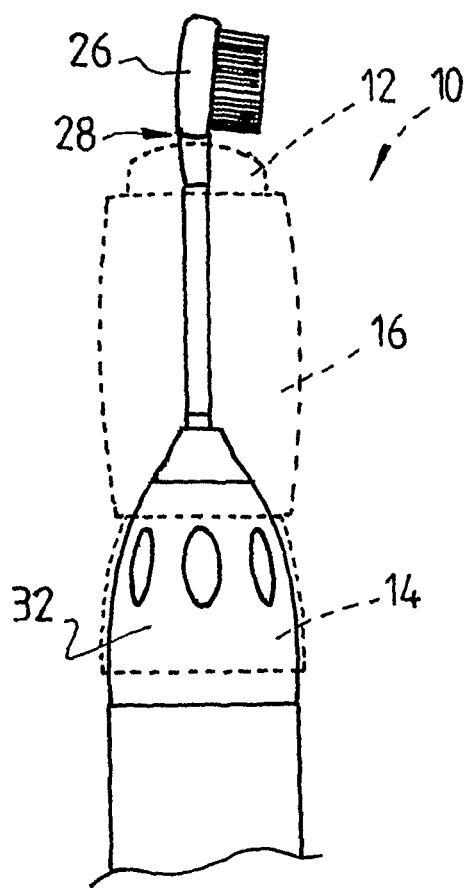
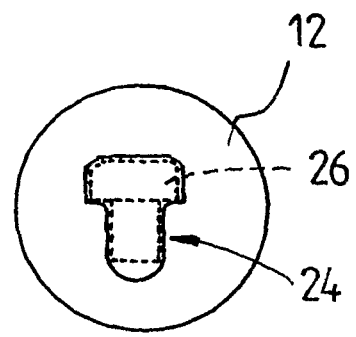
FIG. 5
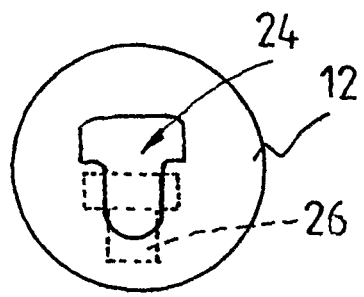
FIG. 6
FIG. 7

TOOTH BRUSH HEAD REMOVAL DEVICE

FIELD OF THE INVENTION

The invention relates to a tooth brush head removal device. In particular, the invention relates to a method of removing a tooth brush head from a body of an electrical tooth brush, to a tooth brush head removal device and to a tooth brush head removal device kit.

BACKGROUND OF THE INVENTION

Electrical toothbrushes have become relatively popular in many regions of the world. By using an electrical toothbrush the task of brushing one's teeth is made relatively easy when compared with traditional manual tooth brushes.

It has been found that a tooth brush head of an electrical tooth brush can become worn. It would be advantageous if the tooth brush head of an electrical tooth brush could be replaced when worn, with a fresh, or replacement tooth brush head.

It is an object of the invention to provide a tooth brush head removal device for removing a tooth brush head of an electrical tooth brush so as to enable the tooth brush head to be replaced after having become worn.

SUMMARY OF THE INVENTION

According to a first aspect of the invention, there is provided a method of removing a tooth brush head from a body of an electrical tooth brush, the method including:

positioning a tooth brush head removal device operatively between a tooth brush head and a body of an electrical tooth brush; and screw threadedly adjusting the tooth brush head removal device to cause a length of the tooth brush head removal device to increase, thereby to cause the tooth brush head to be removed from the body of the electrical tooth brush.

Positioning a tooth brush head removal device operatively between a tooth brush head and a body of an electrical tooth brush may include passing the tooth brush head through the tooth brush head removal device.

Positioning a tooth brush head removal device operatively between a tooth brush head and a body of an electrical tooth brush may include engaging a neck portion of the tooth brush head with a tooth brush head engaging member of the tooth brush head removal device after the tooth brush head has been passed through the tooth brush head removal device.

Engaging a neck portion of the tooth brush head with the tooth brush head engaging member of the tooth brush head removal device may include passing the tooth brush head through a generally key hole shaped aperture defined in the tooth brush head engaging member and displacing the tooth brush head removal device laterally relative to the tooth brush head thereby to engage the neck portion of the tooth brush head in a narrow portion of the generally key hole shaped aperture.

Screw threadedly adjusting the tooth brush head removal device to cause a length of the tooth brush head removal device to increase, thereby to cause the tooth brush head to be removed from the body of the electrical tooth brush, may include angularly displacing a screw threaded member of the tooth brush head removal device relative to the tooth brush head engaging member.

The tooth brush head removal device may include a seat member for seating against a body of an electrical tooth brush, the tooth brush head engaging member and the seat member being screw threadedly engaged with the screw threaded member, screw threadedly adjusting the tooth brush head removal device to cause a length of the tooth brush head removal device to increase, thereby to cause the tooth brush head to be removed from the body of the electrical tooth brush, then including causing the tooth brush head engaging member to displace away from the seat member in response to angularly displacing the screw threaded member.

A tooth brush head removal device including:

a tooth brush head engaging member;

a seat member for seating against a body of an electrical tooth brush; and a screw-threaded member positioned operatively between the tooth brush head engaging member and the seat member, so as to cause the tooth brush head engaging member to displace relative to the seat member in response to angular displacement of the screw-threaded member, such that, in use, the tooth brush head engaging member can be engaged with a tooth brush head of an electrical tooth brush, the seat member can be seated against a body of the electrical tooth brush and the screw threaded member can be displaced angularly thereby to cause the tooth brush head to be removed from the body of the electrical tooth brush.

The tooth brush head removal device may be elongate, the tooth brush head engaging member being positioned at one end, the seat member being positioned at an opposed end.

The screw threaded member may be in the form of a barrel defining an internally screw threaded portion screw threadedly engaged with a screw threaded portion of the tooth brush head engaging member.

The screw threaded member may define another internally screw threaded portion screw threadedly engaged with a screw threaded portion of the seat member.

The tooth brush head engaging member and the seat member may be operatively connected to each other to inhibit angular displacement relative to each other and to permit linear displacement relative to each other.

The screw threaded portions of the barrel may be arranged to cause the tooth brush head engaging member and the seat member to displace away from each other when the barrel is displaced angularly in one direction and to displace toward each other when the barrel is displaced angularly in an opposed direction.

The tooth brush head engaging member may define an aperture arranged to permit a tooth brush head to be passed there through and to engage a neck portion of the tooth brush head.

The aperture may be generally key-hole shaped.

The tooth brush head removal device may define an internal passage and a mouth defined by the seat member to enable the tooth brush head to be passed through the mouth of the seat member, along the passage and through the aperture in the tooth brush head engaging member.

According to another aspect of the invention, there is provided a tooth brush head removal device kit including:

a tooth brush head removal device as described above; and at least one tooth brush head replacement.

BRIEF DESCRIPTION OF THE DRAWINGS

Embodiments of the invention will now be described, by way of example, with reference to the accompanying diagrammatic drawings, in which:

FIG. 5 shows a schematic plan view of a tooth brush head engaging member of the tooth brush head removal device shown in FIG. 1, a tooth brush head being passed through a generally key hole shaped aperture in the tooth brush head engaging member;

FIG. 6 corresponds to FIG. 5, and shows the tooth brush head in an engaged position in the key hole shaped aperture;

FIG. 7 shows a schematic side view of part of an electrical tooth brush, the tooth brush head removal device being positioned on the electrical tooth brush in a position to remove a tooth brush head of the electrical tooth brush.

DETAILED DESCRIPTION OF PREFERRED EMBODIMENTS

Figure 1:
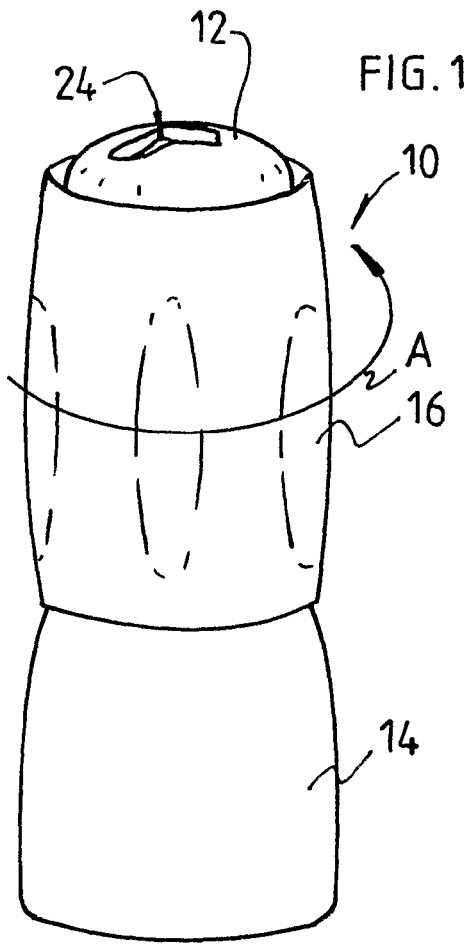
FIG. 1 shows a schematic three dimensional side view of a tooth brush head removal device in accordance with an embodiment of the invention, the tooth brush head removal device being in a retracted condition.

Referring to FIGS. 1 to 4 of the drawings, a tooth brush head removal device, in accordance with an embodiment of the invention, is generally indicated by reference numeral 10.

The tooth brush head removal device 10 includes a tooth brush head engaging member 12 and a seat member 14. The seat member 14 is arranged to seat against a body of an electrical tooth brush, as will be described in greater detail below.

The tooth brush head removal device 10 further includes a screw-threaded member 16 positioned between the tooth brush head engaging member 12 and the seat member 14. The screw threaded member 16 cooperates with the tooth brush head engaging member 12 and the seat member 14 to cause the tooth brush head engaging member 12 and the seat member 14 to displace axially relative to each other in response to angular displacement of the screw threaded member 16 relative to the tooth brush head engaging member 12 and the seat member 14. In use, the tooth brush head engaging member 12 can be engaged with a tooth brush head of an electrical tooth brush, the seat member 14 can be seated against a body of the electrical tooth brush and the screw threaded member 16 can be displaced angularly thereby to cause the tooth brush head to be removed from the body of the electrical tooth brush.

Figure 2:
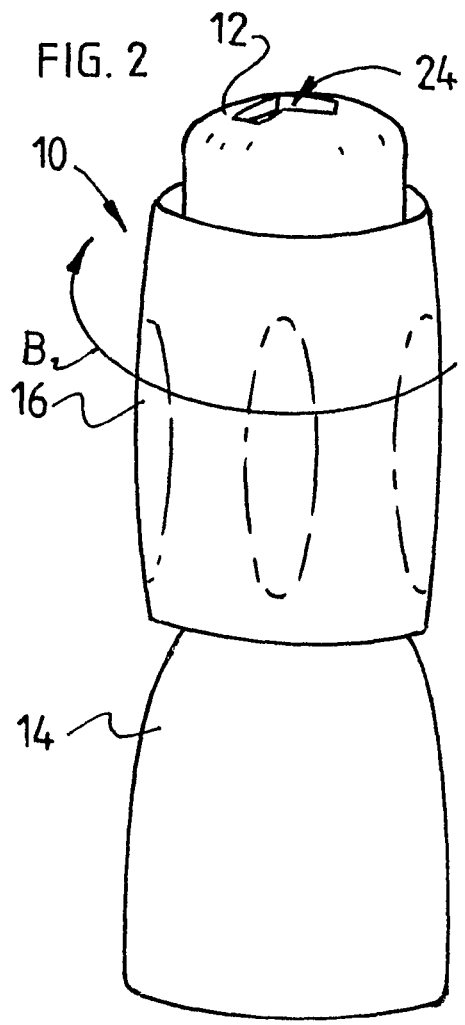
FIG. 2 shows a schematic three dimensional side view of the tooth brush head removal device shown in FIG. 1, the tooth brush head removal device being in an extended condition.
Figure 3:
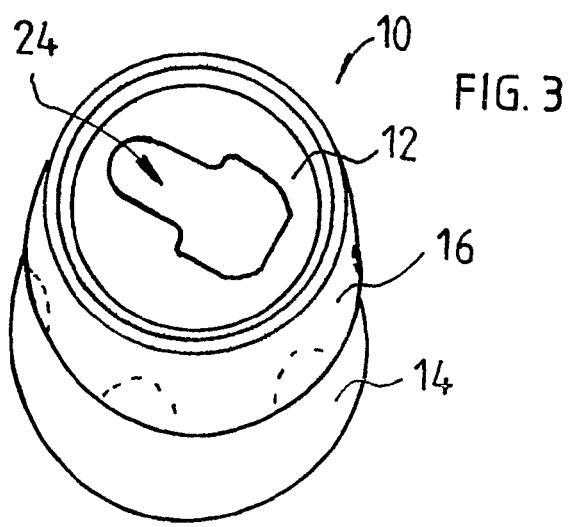
FIG. 3 shows a schematic three dimensional plan view of the tooth brush head removal device shown in FIG. 1.

In FIG. 1, the tooth brush head removal device 10 is in a retracted condition in which the tooth brush head engaging member 12 is positioned relatively close to the seat member 14. By angularly displacing the screw-threaded member 16, as indicated by arrow A, the tooth brush head engaging member 12 and the seat member 14 are displaced apart, as indicated in FIG. 2. By then angularly displacing the screw-threaded member 16 in an opposed direction, as indicated by arrow B, the tooth brush head engaging member 12 and the seat member 14 are displaced toward each other, as indicated in FIG. 1.

The tooth brush head removal device 10 is elongate. The tooth brush head engaging member 12 is positioned at one end and the seat member 14 is positioned at an opposed end.

Figure 4:
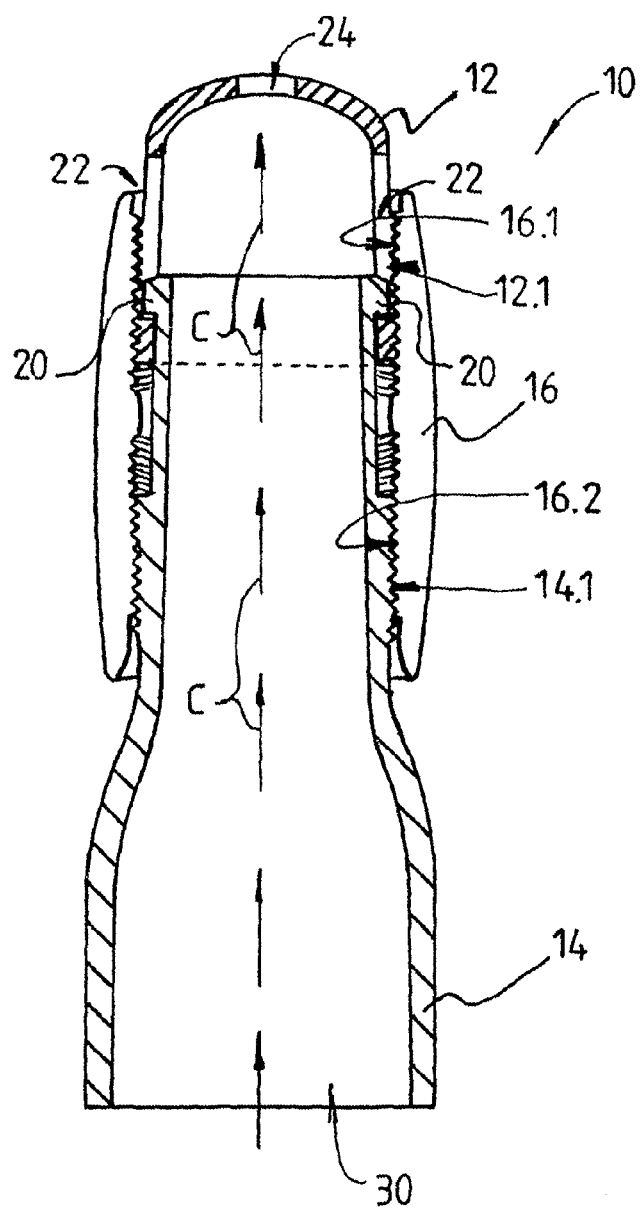
FIG. 4 shows a schematic cross sectional side view of the tooth brush head removal device shown in FIG. 1.

As can best be seen in FIG. 4 of the drawings, in which like reference numerals have been used to designate similar parts, or features, unless otherwise stated, the screw threaded member 16 is in the form of a barrel defining an internally screw threaded portion 16.1. The internally screw threaded portion 16.1 is screw threadedly engaged with a screw threaded portion 12.1 of the tooth brush head engaging member 12.

The screw threaded member 16 defines another internally screw threaded portion 16.2 screw threadedly engaged with a screw threaded portion 14.1 of the seat member 14.

The tooth brush head engaging member 12 and the seat member 14 are operatively connected to each other to inhibit angular displacement relative to each other and to permit linear, or axial, displacement relative to each other. To this end, the seat member 14 defines two diametrically opposes protrusions 20 which ride linearly in slots 22 defined by the tooth brush head engaging member 12.

The screw threaded portions 16.1, 16.2 of the barrel 16 are arranged to cause the tooth brush head engaging member 12 and the seat member 14 to displace away from each other when the barrel 16 is displaced angularly in one direction and to displace toward each other when the barrel 16 is displaced angularly in an opposed direction, as can best be seen with reference to FIGS. 1 and 2 of the drawings. Accordingly, one of the screw threaded portions 16.1, 16.2 can define a clockwise screw thread and the other of the screw threaded portions 16.1, 16.2 can then define an anti-clockwise screw thread.

As can best be seen with reference to FIGS. 5 to 7 of the drawings, in which like reference numerals have been used to designate similar parts, or features, unless otherwise stated, the tooth brush head engaging member 12 defines an aperture 24 arranged to permit a tooth brush head 26 to be passed there through and to engage a neck portion 28 of the tooth brush head 26. Advantageously, the aperture 24 is generally key-hole shaped.

The tooth brush head removal device 10 defines an internal passage, as indicated by arrows C and a mouth 30 defined by the seat member 14. The tooth brush head 26 can be passed through the mouth 30 of the seat member 14, along the passage C and through the aperture 24 in the tooth brush head engaging member 12.

To engage the neck portion 28 of the tooth brush head 26 with the tooth brush head engaging member 12 the tooth brush head 26 is passed through the aperture 24 and is then displaced laterally relative to tooth brush head engaging member 12 thereby to cause the neck portion 28 of the tooth brush head 26 to be engaged in a narrow portion of the generally key hole shaped aperture 24.

In this way, the tooth brush head removal device 10 can be mounted on an electrical tooth brush as indicated in dashed lines in FIG. 7. The seat member 14 then seats against a body 32 of the electrical tooth brush. The screw threaded member 16 can then be displaced angularly to cause the tooth brush head engaging member 12 to extend from the seat member 14 thereby to cause the tooth brush head 26 to be removed from the body 32 of the electrical tooth brush.

Figure 8:
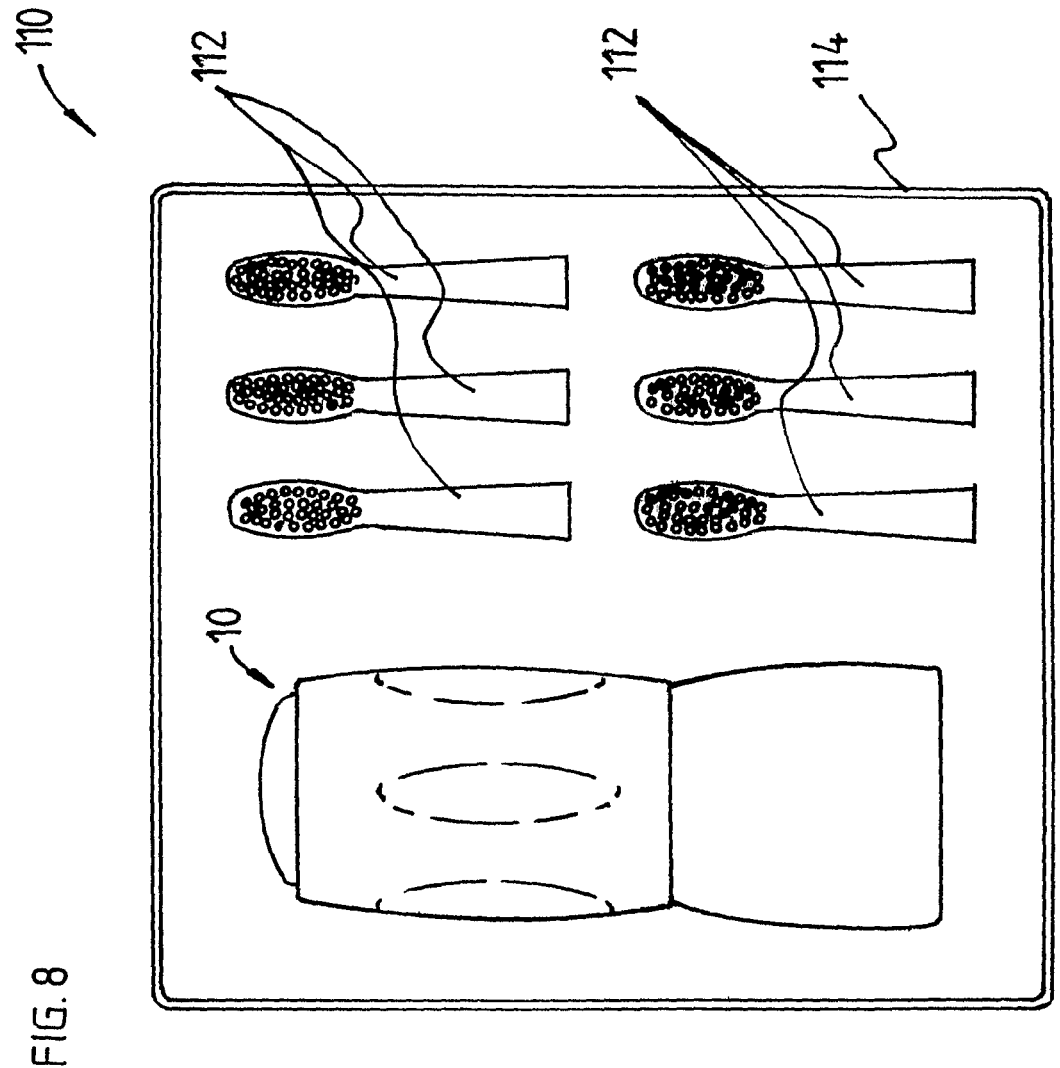
FIG. 8 shows a schematic plan view of a tooth brush head removal device kit in accordance with an embodiment of the invention.

Conveniently, as can best be seen with reference to FIG. 8 of the drawings, a tooth brush head removal device kit, as generally indicated by reference numeral 110, can be provided. The kit 110 can includes a tooth brush head removal device 10 and at least one, in this case six, tooth brush head replacements 112. One of the tooth brush head replacements 112 can then be used after the tooth brush head 26 is removed from the body 32 of the electrical tooth brush. In this way, a used and worn tooth brush head of an electrical tooth brush can be removed and replaced with a new tooth brush head. Conveniently, the tooth brush head replacements 112 can be provided in an appropriate container in a manner similar to disposable shaving blades. Instead, a container 114 can be provided for housing, or containing, the tooth brush head removal device 10 and the tooth brush head replacements 112.

The invention claimed is:

1. An elongate tooth brush head removal device including:
a tooth brush head engaging member positioned at one end of said brush head removal device;
a seat member for seating against a body of an electrical tooth brush positioned at an opposed end of said brush head removal device;
and a screw-threaded member in the form of a barrel defining an internally screw threaded portion screw threadedly engaged, with a first screw threaded portion of said tooth brush head engaging member, and a second internally screw threaded portion threadedly engaged with a screw threaded portion of said seat member, said screw-threaded member positioned operatively between said tooth brush head engaging member and said seat member, so as to cause the tooth brush head engaging member to displace relative to the seat member in response to angular displacement of the screw-threaded member, such that, in use, said tooth brush head engaging member can be engaged with a tooth brush head of an electrical tooth brush, said seat member can be seated against a body of the electrical tooth brush and the screw threaded member can be displaced angularly thereby to cause the tooth brush head to be removed from the body of the electrical tooth brush.

2. The tooth brush head removal device as claimed in claim 1, in which said tooth brush head engaging member and said seat member are operatively connected to each other to inhibit angular displacement relative to each other and to permit linear displacement relative to each other.

3. The tooth brush head removal device as claimed in claim 2, in which the screw threaded portions of the barrel are arranged to cause said tooth brush head engaging member and said seat member to displace away from each other when the barrel is displaced angularly in one direction and to displace toward each other when the barrel is displaced angularly in an opposed direction.

4. The tooth brush head removal device as claimed in claim 3, in which said tooth brush head engaging member defines an aperture arranged to permit a tooth brush head to be passed there through and to engage a neck portion of the tooth brush head.

5. The tooth brush head removal device as claimed in claim 4 in which the aperture is generally key-hole shaped.

6. The tooth brush head removal device as claimed in claim 4 or claim 5, in which the tooth brush head removal device defines an internal passage and a mouth defined by the seat member to enable the tooth brush head to be passed through the mouth of the seat member, along the passage and through the aperture in the tooth brush head engaging member.

* * * * *